US012653590B2

(12) United States Patent
Grossman et al.

(10) Patent No.: US 12,653,590 B2
(45) Date of Patent: Jun. 16, 2026

(54) DETACHABLE BONE FIXATION DEVICE AND RELATED METHODS

(71) Applicant: Surgical Design Innovations, LLC, Johnston, IA (US)

(72) Inventors: Jordan Grossman, Akron, OH (US); Shannon M. Rush, San Jose, CA (US); Michael Lee, Johnston, IA (US); Troy J. Boffeli, Woodbury, MN (US); Mark Hardy, Lakewood, OH (US)

(73) Assignee: Surgical Design Innovations, LLC, Johnston, IA (US)

( * ) Notice: Subject to any disclaimer, the term of this patent is extended or adjusted under 35 U.S.C. 154(b) by 246 days.

(21) Appl. No.: 18/327,271

(22) Filed: Jun. 1, 2023

(65) Prior Publication Data

US 2024/0122635 A1 Apr. 18, 2024

Related U.S. Application Data

(60) Provisional application No. 63/347,611, filed on Jun. 1, 2022.

(51) Int. Cl.
*A61B 17/86* (2006.01)
*A61B 17/88* (2006.01)
*A61B 17/56* (2006.01)

(52) U.S. Cl.
CPC ...... *A61B 17/8615* (2013.01); *A61B 17/8635* (2013.01); *A61B 17/8888* (2013.01); *A61B 2017/564* (2013.01)

(58) Field of Classification Search
CPC ......................... A61B 17/8615; A61B 17/8888
See application file for complete search history.

(56) References Cited

U.S. PATENT DOCUMENTS 1,360,500 A    11/1920   Coll
2,723,694 A    11/1955   Ross
(Continued)

FOREIGN PATENT DOCUMENTS

CN    108542487 A    9/2018
CN    113081218 A    7/2021
(Continued)

OTHER PUBLICATIONS

"4.5 Cannulated Screw" TIPMED, https://www.omnia-health.com/product/45-cannulated-screw.

*Primary Examiner* — Olivia C Chang
(74) *Attorney, Agent, or Firm* — Fredrikson & Byron, P.A

(57) ABSTRACT

Various bone fixation device embodiments include both a fixation device (such as a screw) and a detachable driver device, with the fixation device having an elongate uncannulated fixation shaft, a sharp distal tip, and a proximal head having a first coupling structure and a proximal flat surface, and the detachable driver device having an elongate driver shaft and a distal head having a second coupling structure and a distal flat surface. Further implementations include a combination device comprising both a detachable driver device and a fixation device, along with related systems and methods. In addition, a stabilization device is provided that can be coupled to a detachable driver device and an attachment device to help maintain the coupling of the driver device and the attachment device and help to maintain the coupling thereof during a procedure.

20 Claims, 11 Drawing Sheets

(56)     References Cited

U.S. PATENT DOCUMENTS

| | | | |
|---|---|---|---|
| 5,364,400 | A | 11/1994 | Rego, Jr. et al. |
| 6,048,344 | A | 4/2000 | Schenk |
| 6,402,757 | B1 | 6/2002 | Moore, III et al. |
| 8,906,075 | B2 | 12/2014 | Conley et al. |
| 8,936,615 | B2 | 1/2015 | Pappalardo et al. |
| 9,370,388 | B2 | 6/2016 | Globerman et al. |
| 2004/0122442 | A1 | 6/2004 | Lewis |
| 2009/0192512 | A1 | 7/2009 | Sommers |
| 2011/0077693 | A1* | 3/2011 | Yu ..................... A61B 17/8615 |
| | | | 606/301 |
| 2012/0029577 | A1 | 2/2012 | Kerr et al. |
| 2014/0364906 | A1 | 12/2014 | Palese et al. |
| 2019/0365422 | A1 | 12/2019 | Biedermann et al. |
| 2021/0282828 | A1 | 9/2021 | Champagne et al. |
| 2021/0361334 | A1 | 11/2021 | Wang |

FOREIGN PATENT DOCUMENTS

| | | |
|---|---|---|
| DE | 102014107882 A1 | 12/2015 |
| WO | 1998019617 | 5/1998 |
| WO | 2022157663 A1 | 7/2022 |

* cited by examiner

10

14

12

16

12A

12B

12C

12D

12E

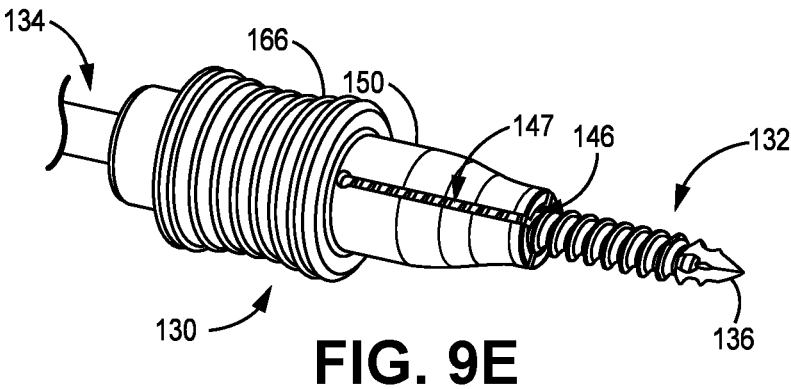
FIG. 9E
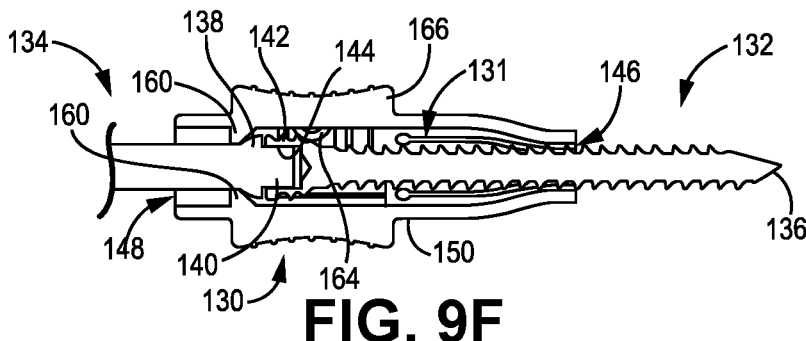
FIG. 9F
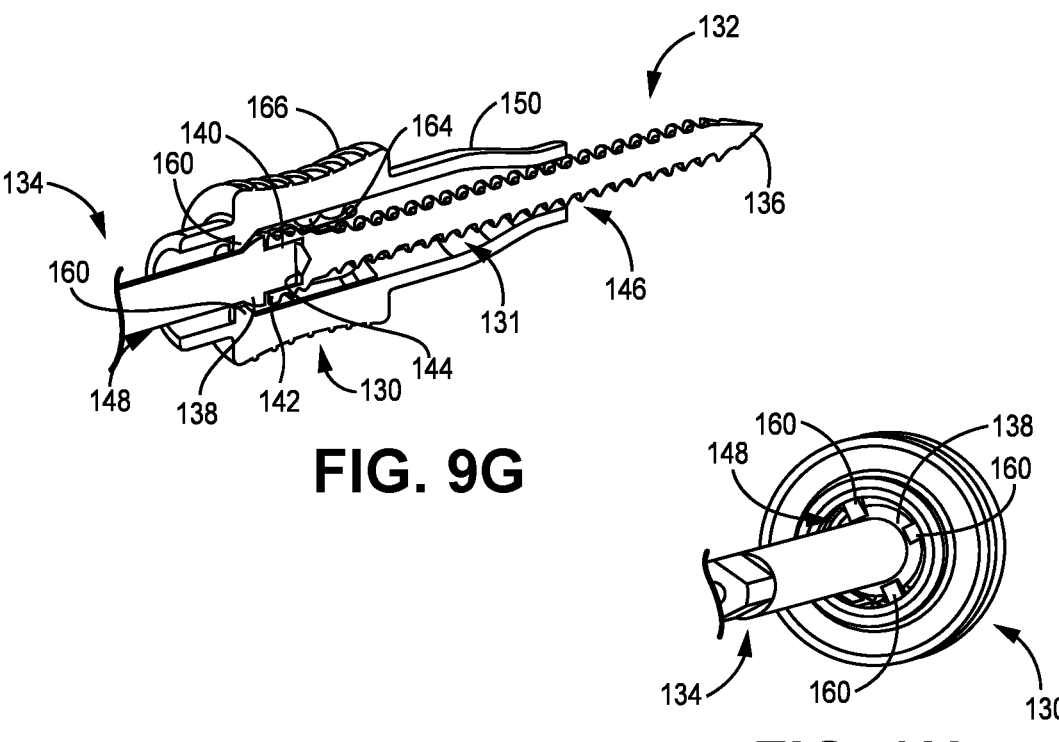
FIG. 9G
FIG. 9H

DETACHABLE BONE FIXATION DEVICE AND RELATED METHODS

CROSS-REFERENCE TO RELATED APPLICATION(S)

This application claims the benefit under 35 U.S.C. § 119(e) to U.S. Provisional Application 63/347,611 filed Jun. 1, 2022 and entitled "Detachable Bone Fixation Wire and Related Methods," which is hereby incorporated herein by reference in its entirety.

FIELD

The various embodiments herein relate to bone fixation devices and procedures for bone fracture stabilization and/or repair, bone joint fusion, plate stabilization, bone reconstruction, and the like.

BACKGROUND

Various temporary and permanent bone fixation devices are used—often in combination—to perform various forms of bone surgeries, including fracture repair and joint fusion. The two most common temporary fixation devices are Kirshner wires ("K-wires") and olive wires, while the most common permanent fixation device is the screw.

A K-wire is a smooth or threaded metal, headless pin with a thin wire design and sharp distal tip that can be inserted into bone via true percutaneous placement (allowing the surgeon to push the pointed tip through the skin directly into the bone) without any pre-drilling or pre-measurement steps and then driven into the bone with a known powered driving device. As such, a K-wire can be quickly inserted in one step. Typically, K-wires are used to temporarily maintain fracture reduction or bone alignment prior to placement of screws, plates, or other permanent fixation devices. In some cases, K-wires can also be left in place as a final fixation implant by either bending or cutting the wire shorter than its original length. In other cases, the proximal end of the K-wire can be allowed to protrude from the bone under the skin or through the skin for later removal.

One disadvantage of a K-wire is that it does not have a head at the proximal end (or along the length) of the wire that engages the outer surface of the target bone like a traditional screw head when the K-wire is fully inserted into the bone. Hence, because it is lacking a head, a K-wire cannot provide any compression between two fragments of bone.

An olive wire is similar to a K-wire in that it is a typically temporary fixation wire having an extended pin/wire shaft (smooth or threaded) with a pointed tip at one end which allows direct drilling into bone without pre-drilling. However, in contrast to a K-wire, an olive wire has a head-like spherical structure (which can mimic an olive shape, which explains the name) along a length of the wire that acts like a screw head. Thus, when the wire is inserted and advanced into the bone, the spherical structure engages the outer surface of the bone and provides compression (a distinct advantage over a K-wire). In addition to bone compression, the spherical structure also allows the olive wire to be used for temporary fixation plate retention (prior to permanent screw placement). Olive wires are typically removed once screws have been inserted, and the residual olive holes may be filled with additional screws depending on plate design and fixation construct. Regardless of the intended use of the olive wire, the length of the wire proximal to the spherical structure (the driver end) is often fairly long (as much as 10 cm in length, according to some examples) for ease of subsequent removal.

One disadvantage of the olive wire is that the driver end protruding from the spherical structure can interfere with or potentially obstruct the surgical procedure. While trimming the wire can reduce the interference, that can leave an exposed and potentially sharp wire tip that carries further risks.

Fixation screws are typically used in conjunction with either K-wires or olive wires to fixate bone. As discussed above, the K-wires or olive wires are typically placed first to temporarily hold bones in place. Both types of wires create small holes and are therefore amenable to removal and reinsertion until the surgeon is satisfied and ready for permanent fixation (using screws, plates, external fixation, or other forms of bone fixation). In contrast, insertion of bone fixation screws requires multiple steps including under drilling, over drilling, counter sinking, depth gauge measurement, tapping and finally screw insertion. Further, cannulated screws require at least the additional step of first placing a guidewire (and in some cases the further steps of capturing an image of the guidewire and measuring the depth thereof) before positioning the cannulated screw over the guidewire. Thus, one disadvantage of bone screws is the number of steps that must be taken to achieve permanent fixation There is a need in the art for an improved fixation device.

BRIEF SUMMARY

Discussed herein are various devices, systems, and methods for performing various bone treatment procedures, including a detachable driver device that is coupleable to a fixation device (or a combination of the two) that can be used in a one-step process for insertion into a target bone. Further embodiments relate to a stabilization device that can be used with the combination of the driver device and fixation device to help maintain the coupling of the driver and fixation devices and stabilize that coupling during use.

In Example 1, a bone fixation device comprises a fixation segment and a detachable driver segment. The fixation segment comprises an elongate uncannulated fixation shaft having a diameter of less than about 5 mm, a sharp distal tip, and a proximal head comprising a first coupling structure, wherein the proximal head has a proximal flat surface comprising a diameter that is greater than the diameter of the elongate fixation shaft. The detachable driver segment comprises an elongate driver shaft having a diameter of less than about 5 mm, and a distal head comprising a distal flat surface and a second coupling structure, wherein the second coupling structure is detachably coupleable with the first coupling structure and the distal flat surface is mateable with the proximal flat surface.

Example 2 relates to the device according to Example 1, wherein the elongate fixation shaft comprises an outer surface having threads.

Example 3 relates to the device according to Example 1, wherein the first coupling structure is a female coupling structure, and wherein the second coupling structure is a male coupling structure.

Example 4 relates to the device according to Example 3, wherein the female coupling structure comprises an opening defined in the proximal flat surface of the proximal head, wherein the male coupling structure comprises a ribbed protrusion extending from the distal flat surface, and wherein the male coupling structure is mateable with the opening defined in the proximal flat surface.

Example 5 relates to the device according to Example 1, wherein the sharp distal tip comprises a self-tapping tip.

Example 6 relates to the device according to Example 1, wherein the proximal head comprises a distal surface having a curved convex shape, and wherein the distal head comprises a proximal surface having a curved convex shape.

Example 7 relates to the device according to Example 1, further comprising a stabilization device removably couple-able to the fixation segment and the detachable driver segment, the stabilization device comprising an elongate body comprising a lumen defined through the elongate body, at least one distal flexible retention structure disposed within the lumen, and at least one proximal flexible retention structure disposed within the lumen proximally of the at least one distal flexible retention structure, wherein the stabilization device is positionable over the fixation segment and the detachable driver segment such that the proximal head and the distal head are disposed within the lumen between the at least one distal flexible retention structure and the at least one proximal flexible retention structure.

In Example 8, a bone fixation device comprises a fixation segment, a detachable driver segment, and a stabilization device. The fixation segment comprises an elongate uncan-nulated threaded fixation shaft having a diameter of less than about 5 mm, a sharp distal tip, and a proximal head comprising a first coupling structure, wherein the proximal head has a proximal flat surface comprising a diameter that is greater than the diameter of the elongate fixation shaft. The detachable driver segment comprises an elongate driver shaft having a diameter of less than about 5 mm, and a distal head comprising a distal flat surface and a second coupling structure, wherein the second coupling structure is detach-ably coupleable with the first coupling structure and the distal flat surface is mateable with the proximal flat surface. The stabilization device comprises an elongate body comprising a lumen defined through the elongate body, at least one distal flexible retention structure disposed within the lumen, and at least one proximal flexible retention structure disposed within the lumen proximally of the at least one distal flexible retention structure. The fixation segment and the detachable driver segment are positionable through the lumen of the stabilization device such that the proximal head and the distal head are coupled together and disposed between the at least one distal flexible retention structure and the at least one proximal flexible retention structure for transport, storage, and use of the bone fixation device.

Example 9 relates to the device according to Example 8, wherein the first coupling structure is a female coupling structure, and wherein the second coupling structure is a male coupling structure.

Example 10 relates to the device according to Example 9, wherein the female coupling structure comprises an opening defined in the proximal flat surface of the proximal head, wherein the male coupling structure comprises a ribbed protrusion extending from the distal flat surface, and wherein the male coupling structure is mateable with the opening defined in the proximal flat surface.

Example 11 relates to the device according to Example 8, wherein the sharp distal tip comprises a self-tapping tip.

Example 12 relates to the device according to Example 8, wherein the proximal head comprises a distal surface having a curved convex shape, and wherein the distal head comprises a proximal surface having a curved convex shape.

In Example 13, a method of implanting a fixation device in a target bone comprises positioning a combination device in a desired location of a target bone. The combination device comprises a fixation device comprising an elongate uncannulated fixation shaft having a diameter of less than about 5 mm and proximal head having a diameter that is greater than the diameter of the elongate fixation shaft, and a detachable driver device. The method further comprises inserting the fixation device into the target bone by rotating the detachable driver device in a first direction with a powered driver tool until the proximal head is flush with an outer surface of the target bone, and detaching the detach-able driver device from the fixation device.

Example 14 relates to the method according to Example 13, wherein the positioning the combination device and the inserting the fixation device are performed without any pre-drilling, tapping, counter-sinking, measuring, or use of a guidewire.

Example 15 relates to the method according to Example 13, further comprising providing the combination device before the positioning the combination device in the desired location of the target bone, wherein the detachable driver device is coupled to the fixation device.

Example 16 relates to the method according to Example 15, further comprising packaging, transporting, and/or stor-ing the combination device while the detachable driver device is coupled to the fixation device.

Example 17 relates to the method according to Example 13, further comprising reattaching the detachable driver device and retracting the fixation device some length in relation to the target bone by rotating the detachable driver device in a second direction.

Example 18 relates to the method according to Example 17, wherein the retracting the fixation device comprise fully retracting the fixation device from the target bone.

Example 19 relates to the method according to Example 13, further comprising positioning the combination device through a stabilization device prior to inserting the fixation device into the target bone, the stabilization device com-prising an elongate body comprising a lumen defined through the elongate body, at least one distal flexible reten-tion structure disposed within the lumen, and at least one proximal flexible retention structure disposed within the lumen proximally of the at least one distal flexible retention structure, wherein the proximal head and the distal head are coupled together and disposed between the at least one distal flexible retention structure and the at least one proximal flexible retention structure.

Example 20 relates to the method according to Example 19, wherein the inserting the fixation device into the target bone further comprises rotating the detachable driver device in the first direction until the proximal head exits the stabilization device.

While multiple embodiments are disclosed, still other embodiments will become apparent to those skilled in the art from the following detailed description, which shows and describes illustrative embodiments. As will be realized, the various implementations are capable of modifications in various obvious aspects, all without departing from the spirit and scope thereof. Accordingly, the drawings and detailed description are to be regarded as illustrative in nature and not restrictive.

BRIEF DESCRIPTION OF THE DRAWINGS

FIG. 9E is an enlarged perspective view of the stabilization device coupled to the combination device of FIG. 9A, according to one embodiment.

FIG. 9F is an enlarged cross-sectional view of the stabilization device coupled to the combination device of FIG. 9A, according to one embodiment.

FIG. 9G is an enlarged cross-sectional perspective view of the stabilization device coupled to the combination device of FIG. 9A, according to one embodiment.

FIG. 9H is an enlarged perspective end view of the proximal end of the stabilization device coupled to the combination device of FIG. 9A, according to one embodiment.

DETAILED DESCRIPTION

The various detachable bone fixation device embodiments herein relate to devices, systems, and methods that include a fixation device and a removably coupleable driver device that can be used in combination to implant the fixation device in a one-step process. According to additional implementations, the devices, systems, and methods herein can also include a stabilization and/or guiding device that can be coupled with a fixation device and removably coupleable driver device such that the stabilization/guiding device helps not only to maintain the coupling of the fixation device and driver device, but also to guide and stabilize the fixation and driver devices as they are used in a one-step bone-related procedure.

In certain implementations, the various fixation and driver devices disclosed or contemplated herein incorporate the key advantages of the three standard bone fixation devices—the K-wire, the olive wire, and the fixation screw—while overcoming several of their disadvantages. The implementations herein provide one-step insertion (unlike the fixation screw), bone compression (unlike the K-wire), elimination of proximal wire sections protruding from the bone/skin (unlike the K-wire or olive wire), simple tightness adjustment (unlike the K-wire or olive wire), simple removal (unlike the K-wire), and optionally being implanted temporarily or permanently (unlike the K-wire or olive wire). Further, the various implementations herein relate to a combination device that includes both a driver device and a fixation device that are removably coupled together prior to use and can be uncoupled as desired.

Figure 1A:
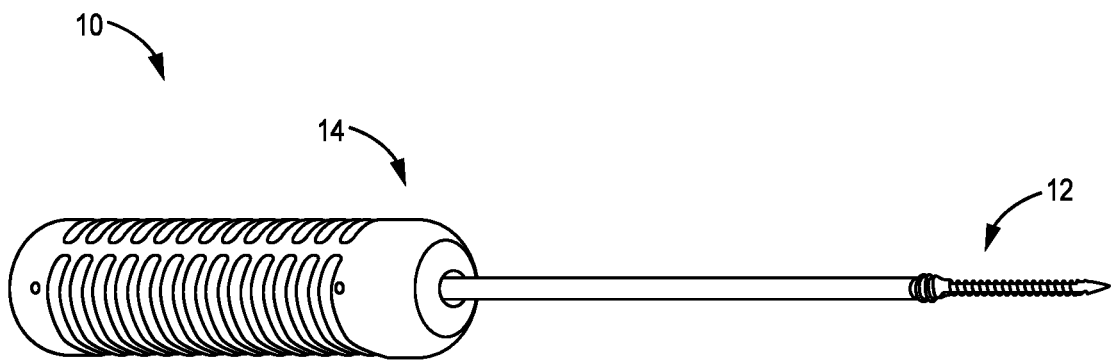
FIG. 1A is a perspective view of a combination device having both a detachable driver device and a fixation device, according to one embodiment.

One embodiment of a combination bone fixation device 10 is shown in FIG. 1A with two parts: an insertable fixation device (or "fixation segment," "fixation screw," or "fixation pin") 12 and a detachable driver device (or "driver segment" or "driver pin") 14 for driving the fixation device 12 into or out of the target bone. The fixation device 12 is a threaded device 12 that can be a screw, pin, wire, rod, or any other similar component for use as a threaded fixation device for easy insertion into a bone. Further, as will be described in additional detail below, some exemplary fixation device implementations 12 as disclosed or contemplated herein can be inserted into bone without the need for any pre-drilling or any other preliminary step for preparing the target area prior to inserting the fixation device 12. In other words, each such fixation device 12 can be inserted into the target area of the bone in a single step.

According to certain implementations, the combination device 10 can be provided with the fixation device 12 and the driver device 14 detachably coupled together for immediate use. Further, in some exemplary embodiments, the combination device 10 can be provided in this coupled configuration in the packaging in which it is delivered to the procedural arena (such as an operating room, for example) such that the fixation segment 12 and driver segment 14 are detachably coupled together when the device 10 is removed from the packaging by the surgeon or other user.

Figure 1B:
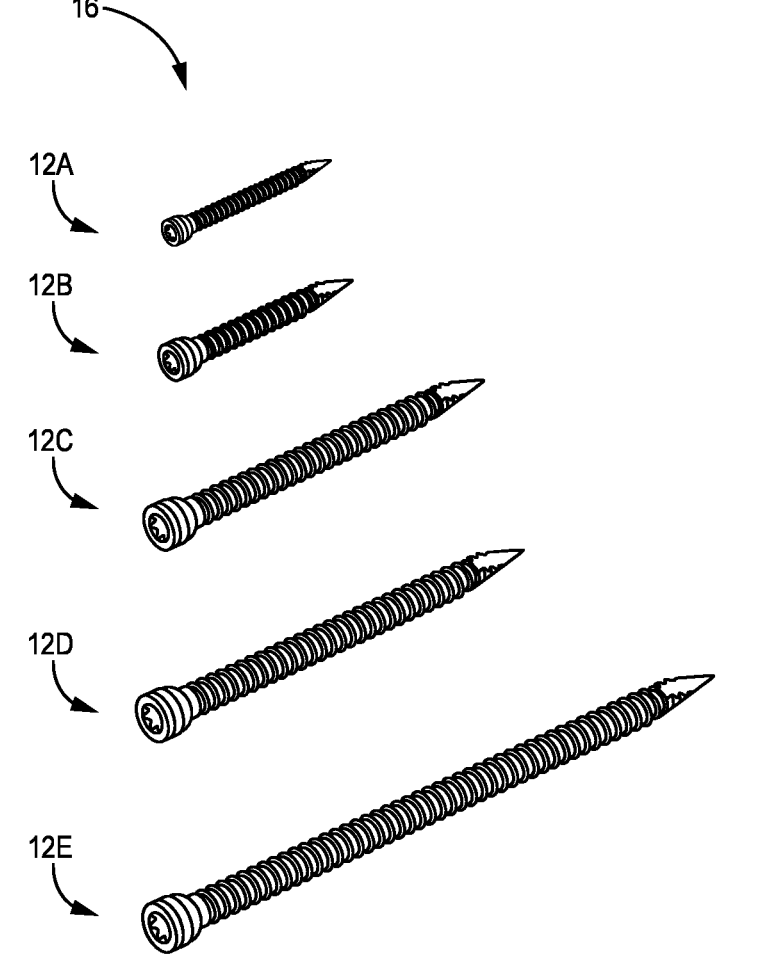
FIG. 1B is a perspective view of a set of fixation devices, according to one embodiment.

As shown in FIG. 1B, certain system embodiments can include a set of fixation devices 16 of differing sizes that is provided along with the driver device 14 (such as the device 14 of FIG. 1A, for example). Thus, in certain examples, the surgeon or other user has access to the driver device 14 and a complete set 16 of fixation devices 12A-12E, with each fixation device 12A-12E being of a different size that might be needed for the specific procedure to be performed. Further, according to various specific exemplary embodiments, the system includes a package that contains the device 14 and the set 16 of fixation devices. Alternatively, the system can include a package that contains the combination device 10 of FIG. 1A (with the driver device 14 already coupled to one fixation device 12) along with a full set of fixation devices 16 that can include devices 12A-12E of differing sizes along with some duplicate devices 12A-12E of the same size.

Figure 2A:
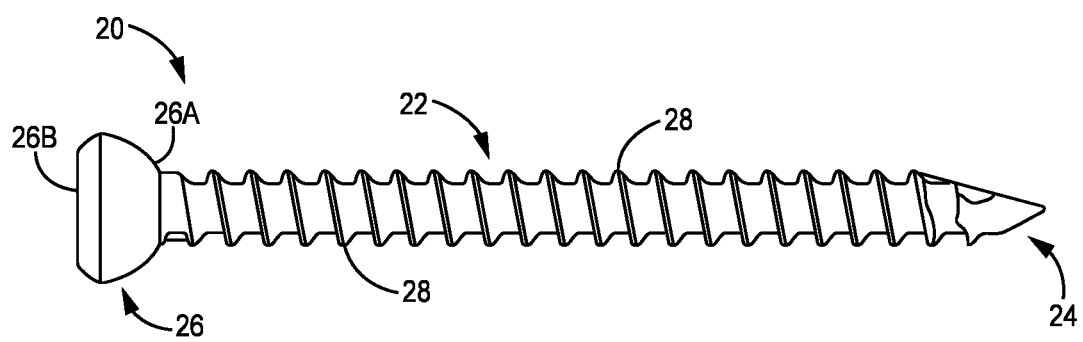
FIG. 2A is a side view of a fixation device, according to one embodiment.
Figure 2B:
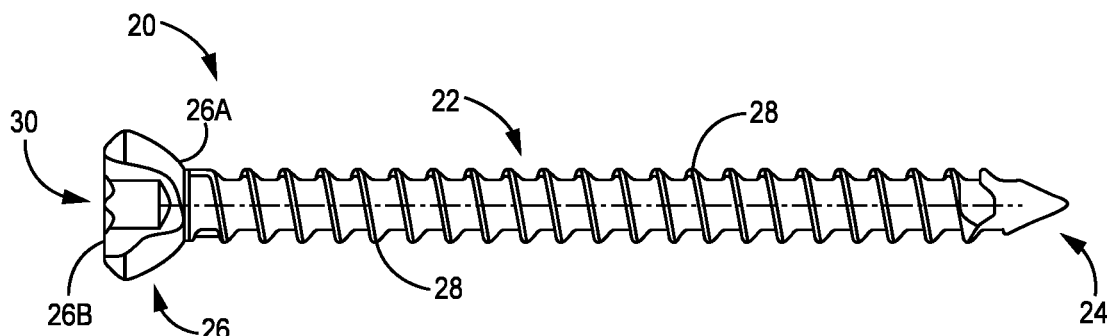
FIG. 2B is a cross-sectional side view of the fixation device of FIG. 2A, according to one embodiment.
Figure 2C:
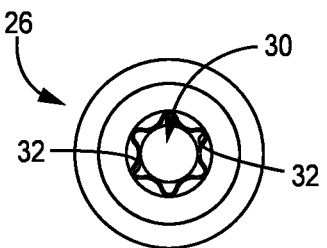
FIG. 2C is an end view of the proximal head of the fixation device of FIG. 2A, according to one embodiment.
Figure 2D:
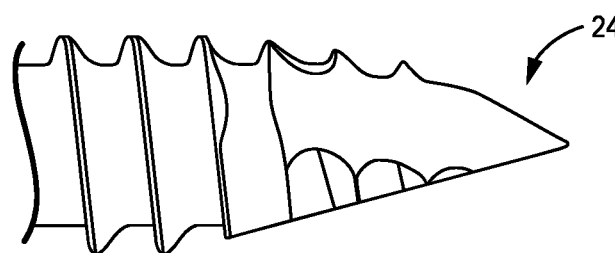
FIG. 2D is an enlarged side view of the distal tip of the fixation device of FIG. 2A, according to one embodiment.
Figure 2E:
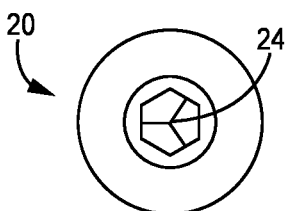
FIG. 2E is an end view of the distal tip of the fixation device of FIG. 2A, according to one embodiment.

As shown in FIGS. 2A-2E, one exemplary fixation device 20 has an elongate shaft 22, a sharp distal tip 24 at the distal end of the shaft 22, and a proximal head 26 at the proximal end thereof. In this embodiment, the device 20 is uncannulated (that is, there is no lumen or cannula defined through the length of the device 20 for purposes of positioning the device 20 over a guidewire). The outer surface of the shaft 16 has threads 28 disposed along an entire length of the shaft 22 (as shown). The distal tip 24 (as best shown in FIGS. 2A and 2D) is sufficiently sharp to allow for insertion through a patient's skin and into the bone without requiring a hole to be formed in the bone first. That is, the tip 24 is a "self-tapping" tip 24 or operates to allow the fixation device 20 to be self-tapping. For example, in certain embodiments, the tip 24 is shaped like a self-tapping tip on a K-wire or Steinmann pin, for example. Such a tip 24 can come in a variety of configurations, including a Trocar tip, a diamond tip, etc. The term "self-tapping" as used herein to describe the tip 24 is intended to mean that the tip 24 is configured to cut through the target bone cortex in the same fashion as a drill bit, K-wire, or olive wire without any prior preparation step (such as pre-drilling or the like) for the target area.

In certain embodiments such as the example depicted in FIGS. 2A and 2B, the proximal head 26 has a curved, convex shape on its distal side 26A and is flat on the proximal side 26B with a female coupling feature 30 defined in the proximal side 26B (as best shown in FIGS. 2B and 2C and discussed in further detail below). In other words, the proximal head 26 is shaped like half of a sphere (or a "half sphere"). In many implementations, the female coupling feature 30 is an opening 30 defined in the proximal side 26B of the head 26 that can receive and detachably mate with a male coupling feature (such as feature 48 discussed below) of a driver device (such as device 40). Alternatively, the proximal head 26 can be any structure with any shape so long as the structure has a larger diameter than the shaft 22, a flat surface on the proximal side 26B of the head 26, and a coupling structure or feature 30 defined therein.

Any of the various fixation device embodiments disclosed or contemplated herein, including the various implementations discussed below, can have the same or similar components, features, and/or functions.

As shown in FIGS. 3A-3D, one exemplary embodiment of a detachable driver device 40 has an elongate shaft 42 with a mateable distal tip 44 at the distal end of the shaft 42. The elongate shaft 42 is typically smooth or substantially smooth. The distal tip 44 can have a head 46 with a male coupling feature 48 associated therewith. More specifically, in the exemplary embodiment as shown, the head 46 has a curved, convex shape on its proximal side 46B and is flat on its distal side 46A with the male coupling feature 48 extending therefrom. In other words, the distal head 46 is shaped like a half of a sphere (or a "half sphere") that mirrors the half sphere shaped proximal head 26 as discussed above. Alternatively, the distal tip 44 can have any structure with any shape so long as the structure has a coupling structure or feature for coupling to the proximal head 26 as discussed in further detail below.

Figures 3A, 3B, 3C, 3D:
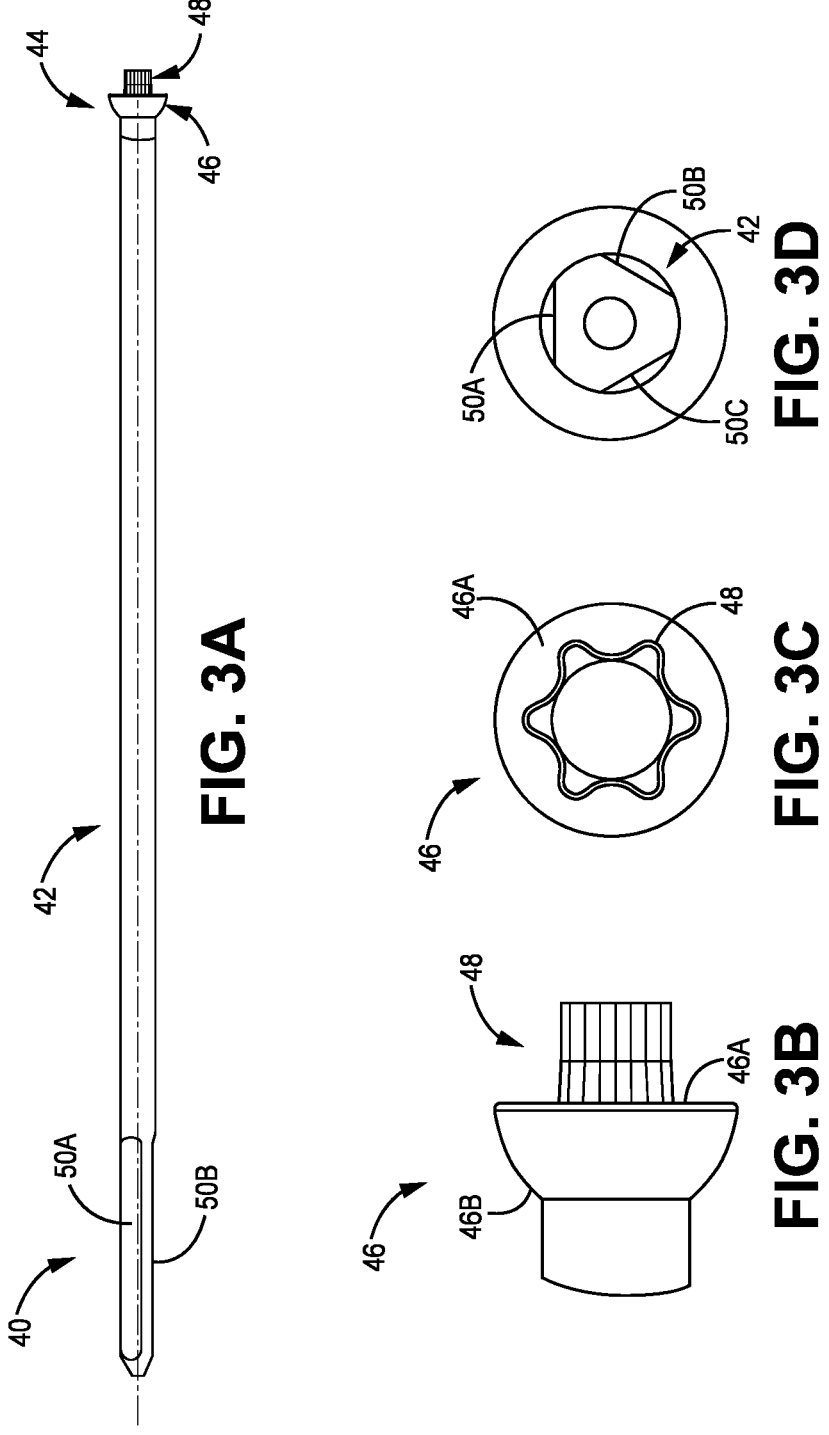
FIG. 3A is a side view of a detachable driver device, according to one embodiment.
FIG. 3B is an enlarged side view of the distal head of the detachable driver device of FIG. 3A, according to one embodiment.
FIG. 3C is an end view of the distal head of the detachable driver device of FIG. 3A, according to one embodiment.
FIG. 3D is an end view of the proximal end of the detachable driver device of FIG. 3A, according to one embodiment.

In accordance with certain implementations, the driver device 40 can also have attachment features 50A-50C defined in a proximal portion of the shaft 42 as shown in FIGS. 3A and 3D. More specifically, in the specific embodiment of FIG. 3D, the shaft 42 has three attachment features 50A-50C defined along a proximal length of the shaft 42. The three attachment features 50A-50C are elongate flat segments 50A-50C defined in the proximal length of the shaft 42. Thus, a known actuable driver apparatus (not shown) can be positioned over the proximal portion of the shaft 42 and attached to the attachment features 50A-50C such that the driver apparatus can cause the shaft 42 to rotate as a result of the attachment to the attachment features 50A-50C.

Any of the various driver device embodiments disclosed or contemplated herein, including the various implementations discussed below, can have the same or similar components, features, and/or functions.

In one exemplary embodiment as shown in FIGS. 2B, 2C, 3B, and 3C, the female coupling feature 30 of the fixation device 20 and the male coupling feature 48 of the driver device 40 are Torx® mateable drive components. That is, the female coupling feature 30 is an opening 30 defined in the proximal side 26B of the head 26 with features 32 defined or disposed on the inner surface of the opening 30 as best shown in FIG. 2C. Similarly, the male coupling feature 48 is a protrusion 48 with features 52 defined or disposed on the outer surface of the protrusion 48 as best shown in FIG. 3C. The features 52 of the protrusion 48 are sized and shaped to mate with the features 32 of the opening 30 when the driver device 40 is coupled with the fixation device 20. More specifically, in this specific implementation, the features 52 are ribs 52 that fit within the features 32 of the opening 30, which are channels 32 sized to receive the ribs 52. Alternatively, the coupling features 30, 48 can be any known coupleable male and female structures, with no limitation on the location of the male and female structures on the insertable fixation device 20 and a detachable driver device 40. In a further alternative, the coupling features on the two coupleable segments 20, 40 can be any known coupling components that allow for coupling and uncoupling of the two segments 20, 40 during use as described herein. Any of the various embodiments disclosed or contemplated herein, including the various implementations discussed below, can have the same or similar coupling features.

In certain implementations, the opposing flat surfaces 26B, 46A of the two heads 26, 46 facilitate and help to stabilize the coupling of the two devices 20, 40. More specifically, as the male coupling feature 48 of the driver device 40 is inserted into the female coupling feature 30 of the fixation device 20 and the distal head 46 is urged distally into contact with the proximal head 26, the flat surface 46A makes contact with the flat surface 26B. Because of the flat surfaces 26B, 46A, when the two heads 26, 46 are in contact, the two devices 20, 40 cannot easily be rotated radially in relation to each other at the junction of the two coupling features 30, 48. That is, the two flat surfaces 26B, 46A facilitate the alignment of the two devices 20, 40 such that the longitudinal axes of each of the device 20, 40 are urged into a co-axial configuration (such as that shown in FIG. 1A, for example) when the two flat surfaces 26B, 46A are in contact with each other. In contrast, if either or both of the surfaces 26B, 46A were to be rounded or convex (in a fashion similar to the surfaces 26A, 46B, for example), the surfaces would not urge the two devices into a co-axial configuration when they are in contact and, in fact, would allow for the two devices to rotate radially in relation to each other at the junction of the two surfaces. Thus, the two mateable flat surfaces 26B, 46A help to prevent the two devices 20, 40 from "tipping" or otherwise moving radially in relation to each other during use. In one exemplary embodiment, each of the two flat surfaces 26B, 46A has a diameter of at least 1.5 mm.

Further, in any of the various embodiments disclosed or contemplated herein in which the distal head (such as head 46) and proximal head (such as head 26) are both shaped like half spheres, when the two heads are paired by coupling the two coupling features (such as features 30, 48), a complete sphere is formed by the two heads and a complete combination device (such as device 10) is formed by the two devices (such as devices 10, 12 or devices 20, 40). The two coupling features 30, 48 are also detachable from each other when the detachable driver device (such as device 14 or 40) is retracted proximally or otherwise manipulated by the user such that the coupling feature 48 is disengaged from the coupling feature 30. Alternatively, the coupling feature 48 can be disengaged from the coupling feature 30 in any known fashion. Any of the various embodiments disclosed or contemplated herein, including the various implementations discussed below, can have the same or similar coupling features.

In accordance with certain implementations, any of the two devices (such as devices 12, 14 or devices 20, 40, for example) can be made of stainless steel or a titanium alloy. In one specific embodiment, the two devices 12, 14 or 20, 40 are made of 316 L surgical stainless steel. Alternatively, the two devices 12, 14 or 20, 40 can be made of any appropriate metal or combination of metals that are used in bone fixation devices.

In some aspects, any of the insertable fixation devices herein (such as devices 12 and 20) can have a length ranging from about 6 mm to about 80 mm. Further, any of the detachable driver devices (such as devices 14 and 40) can have a length ranging from about 10 cm to about 20 cm. In addition, each of the elongate shaft (such as shaft 22) of the fixation device (such as device 12 or 20) and the elongate shaft (such as shaft 42) of the driver device (such as device 14 or 40) can have a diameter ranging from about 1.2 mm to about 4 mm. In addition, each of the proximal head (such as head 26) of the fixation device (such as device 12 or 20)

and the distal head (such as head 46) of the driver device (such as device 14 or 40) can have a diameter ranging from about 3 mm to about 6 mm at its greatest diameter.

Figures 4A, 4B, 5A, 5B, 5C:
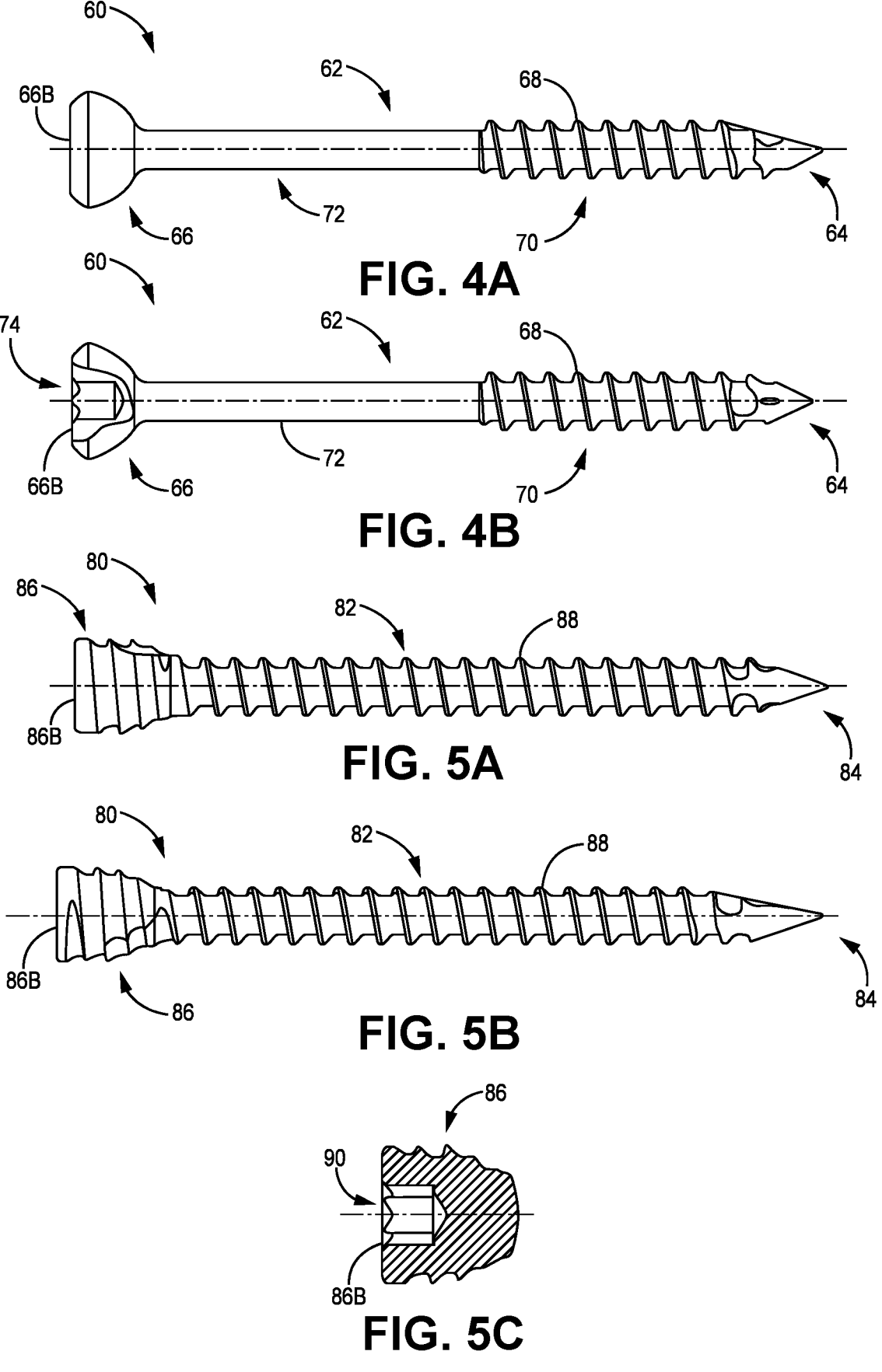
FIG. 4A is a side view of a fixation device having a shaft with a threaded portion and an unthreaded portion, according to one embodiment.
FIG. 4B is a cross-sectional side view of the fixation device of FIG. 4A, according to one embodiment.
FIG. 5A is a side view of a fixation device having threads disposed around the proximal head, according to one embodiment.
FIG. 5B is another side view of the fixation device of FIG. 5A, according to one embodiment.
FIG. 5C is an enlarged, cross-sectional side view of the proximal head of the fixation device of FIG. 5A, according to one embodiment.

In certain implementations, one or more of the fixation devices used within the systems described or contemplated herein can have threads disposed or defined along only a portion of the length thereof. For example, in the embodiment of FIGS. 4A-4B, the fixation device 60 has an uncannulated elongate shaft 62, a sharp distal tip 64 at the distal end of the shaft 62, and a proximal head 66 at the proximal end thereof. Except as discussed herein, the components and features of the fixation device 60 are substantially similar and function in substantially the same way as the other fixation device embodiments herein. In this exemplary implementation, the outer surface of the shaft 62 has threads 68 disposed along a threaded portion 70 of the shaft 62 (as shown) and also has a portion 72 without threads 68. More specifically, the threaded portion 70 in this exemplary embodiment is a distal threaded portion 70 of the shaft 62, while the non-threaded or "smooth" portion 72 is a proximal portion 72 of the shaft 62. Even more specifically, the threads 68 are disposed along a distal half 70 of the shaft 62 and the smooth portion 72 is the proximal half 72 of the shaft 62. Alternatively, the threaded portion 70 can be any portion of the shaft 62 that is less than the entire length of the shaft 62. Further, the proximal head 66 is shaped like a half sphere with a flat surface on the proximal side 66B substantially similar to the proximal head 26 discussed above. Alternatively, the proximal head 66 can be any structure with any shape so long as the structure has a larger diameter than the shaft 62, a flat surface on the proximal side 66B of the head 66, and a coupling structure or feature 74 defined therein.

In further embodiments, one or more of the fixation devices used within the systems described or contemplated herein can have threads that are disposed along the entire length of the device, including not only the shaft, but also the proximal head. For example, in the embodiment of FIGS. 5A-5C, the fixation device 80 has an uncannulated elongate shaft 82, a sharp distal tip 84 at the distal end of the shaft 82, and a proximal head 86 at the proximal end thereof. Except as discussed herein, the components and features of the fixation device 80 are substantially similar and function in substantially the same way as the other fixation device embodiments herein. In this exemplary implementation, the device 80 has threads 88 disposed around the outer surface of the shaft 82 and the proximal head 86 as shown. More specifically, the threads 88 in this exemplary embodiment are disposed along the entire length of the device 80, including the shaft 82 and the proximal head 86. Alternatively, the device 80 can have threads 88 disposed around the entire proximal head 86 but only a portion of the shaft 82 in a fashion similar to the device 70 described above. Further, the proximal head 86 has a flat surface on the proximal side 86B substantially similar to the proximal heads 26, 76 discussed above. Alternatively, the proximal head 86 can be any structure with any shape so long as the structure has a larger diameter than the shaft 82, a flat surface on the proximal side 86B of the head 86, threads 88 disposed around the proximal head 86, and a coupling structure or feature 90 defined therein.

Another implementation of a combination bone fixation device 100 is shown in FIGS. 6-8B with an insertable fixation device 102 and a detachable driver device 104 for driving the fixation device 102 into or out of the target bone. Except as expressly set forth herein, the various components, features, and functions of the fixation device 102 and the driver device 104 can be the same or substantially similar to the fixation and driver device embodiments disclosed or contemplated elsewhere herein, including the fixation device 12, 20, 60, 80 and the driver device 14, 40 embodiments described in detail above.

In the specific exemplary embodiment as shown in FIGS. 6-8B, the combination device 100 can be provided with the fixation device 102 and the driver device 104 detachably coupled together for immediate use in a fashion similar to that described above with respect to fixation device 12 and driver device 14. Further, in certain implementations, the device 100 can be part of a system having multiple fixation devices (such as device 12) of differing sizes in a fashion similar to that described above with respect to FIG. 1B.

Figures 6, 7:
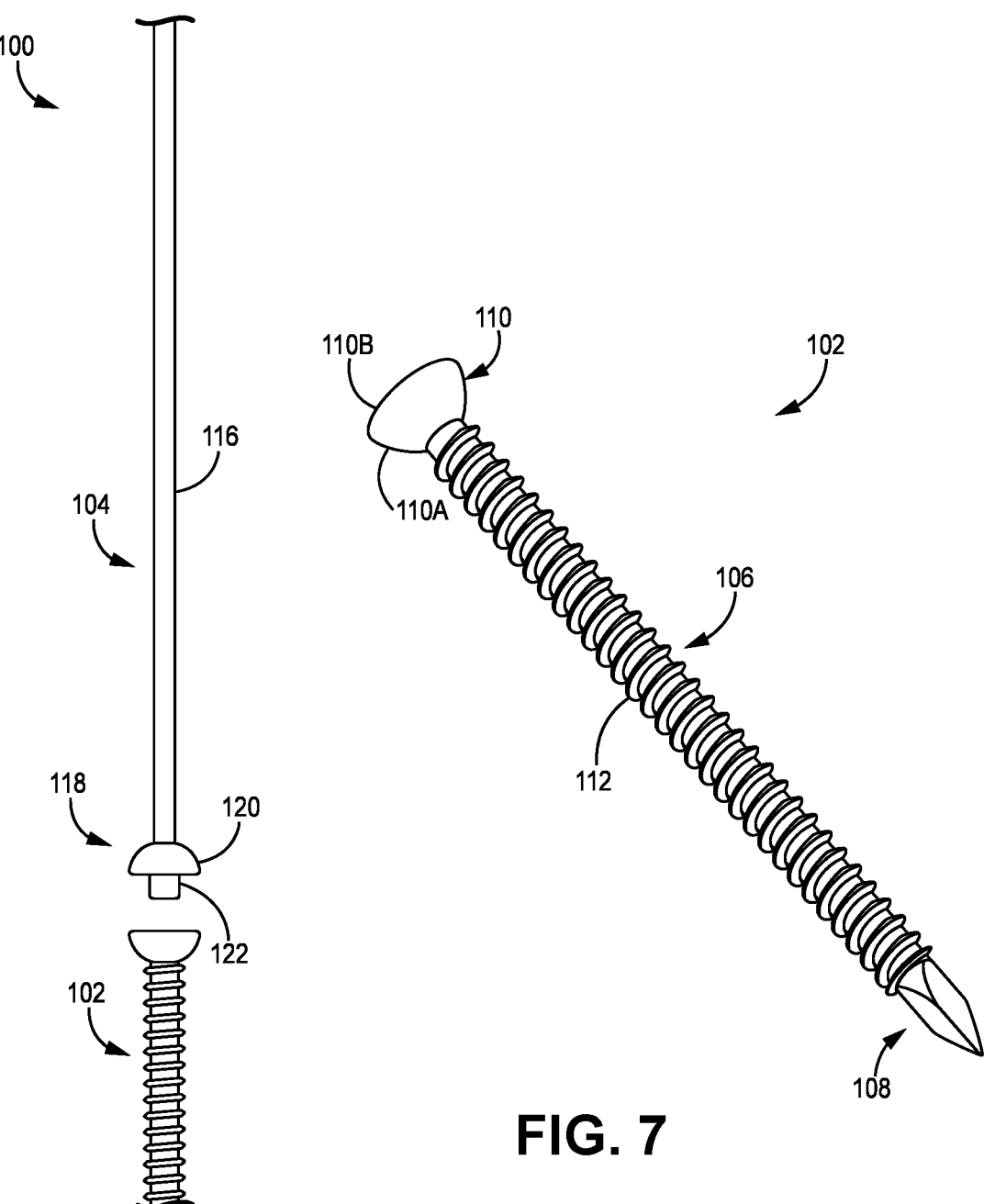
FIG. 6 is a side view of a combination device having a detachable driver device and a fixation device, according to one embodiment.
FIG. 7 is a perspective view of the fixation device of FIG. 6, according to one embodiment.
Figure 8A:
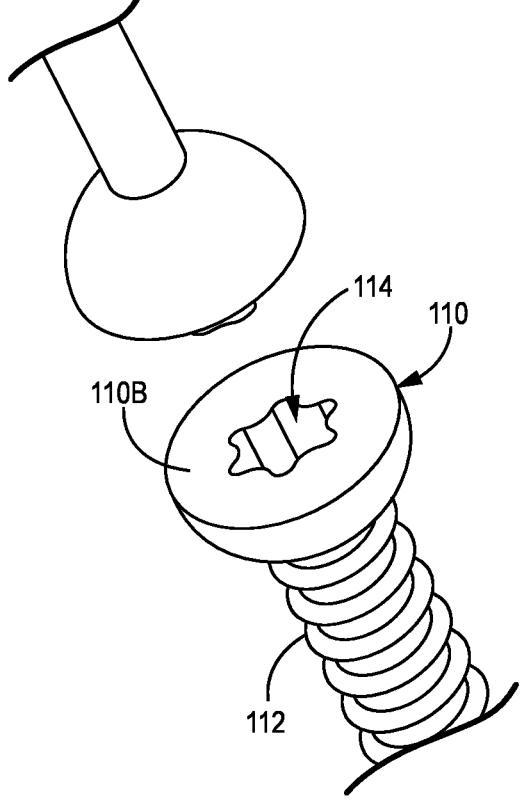
FIG. 8A is an enlarged perspective view of the proximal head of the fixation device and the distal head of the detachable driver device of FIG. 6, according to one embodiment.

As best shown in FIG. 7, the exemplary fixation device 102 has an uncannulated elongate shaft 106, a sharp distal tip 108 at the distal end of the shaft 106, and a proximal head 110 at the proximal end thereof. The outer surface of the shaft 106 has threads 112 disposed along an entire length of the shaft 106 (as shown). The distal tip 108 is a self-tapping tip 108 or operates to allow the fixation device 102 to be self-tapping in a fashion similar to the device 20 discussed above. In certain embodiments such as the example depicted in FIGS. 7, 8A, and 8B, the proximal head 110 has a half-sphere shape with a curved, convex shape on its distal side 110A and is flat on the proximal side 110B with a female coupling feature 114 defined in the proximal side 110B (as best shown in FIG. 8A) in a fashion similar to the proximal head 26 discussed in detail above. Alternatively, the proximal head 110 can be any structure with any shape so long as the structure has a larger diameter than the shaft 106, a flat surface on the proximal side 110B of the head 110, and a coupling structure or feature 114 defined therein.

Figure 8B:
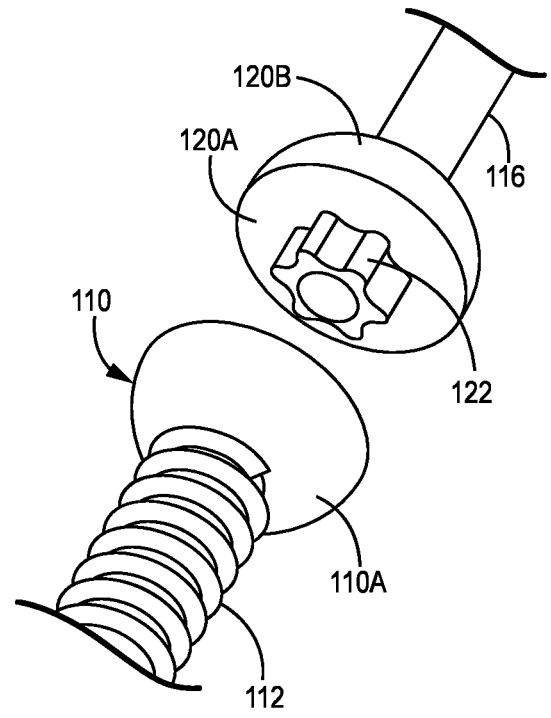
FIG. 8B is another enlarged perspective view of the proximal head of the fixation device and the distal head of the detachable driver device of FIG. 6, according to one embodiment.

As best shown in FIGS. 6 and 8B, one exemplary embodiment of a detachable driver device 104 has an elongate shaft 116 with a mateable distal tip 118 at the distal end of the shaft 116 that has a head 120 with a male coupling feature 122 associated therewith. In the exemplary embodiment as shown, the head 120 has a curved, convex shape on its proximal side 120B and is flat on its distal side 120A with the male coupling feature 122 extending therefrom in a fashion similar to the distal head 46 discussed in detail above. Alternatively, the distal tip 118 can have any structure with any shape so long as the structure has a coupling structure or feature for coupling to the proximal head 110 as discussed in further detail below. In accordance with certain implementations, the driver device 104 can also have attachment features (not shown) defined in or disposed on a proximal portion of the shaft 116 similar to attachment features 50A-50C discussed above.

In one exemplary embodiment as best shown in FIGS. 8A and 8B, the female coupling feature 114 of the fixation device 102 and the male coupling feature 122 of the driver device 104 can be Torx® mateable drive components in a fashion similar to the female 30 and male 48 coupling features discussed above. Alternatively, the coupling features 114, 122 can be any known coupleable male and female structures, with no limitation on the location of the male and female structures on the insertable fixation device 102 and a detachable driver device 104.

In certain implementations, the opposing flat surfaces 110B, 120A of the two heads 110, 120 facilitate and help to stabilize the coupling of the two devices 102, 104 in the same or a similar way to that described above with respect to the flat surfaces 26B, 46A discussed above. Further, the distal head 120 and proximal head 110 are both shaped like half spheres such that when the two heads 120, 110 are paired by coupling the two coupling features 114, 122, a complete sphere is formed by the two heads 120, 110 and a complete combination device (such as device 100) is formed by the two devices 102, 104 in a fashion similar to that described above. The two coupling features 114, 122 are also detachable from each other when the detachable driver device 104 is retracted proximally or otherwise manipulated by the user such that the coupling feature 122 is disengaged from the coupling feature 114 in a fashion similar to that described above as well.

In accordance with certain implementations, the two devices 102, 104 can be made of any metal or combination of metals as discussed above with the previous embodiments and can have the same or similar dimensions.

In use, any of the various fixation device embodiments disclosed or contemplated herein can be used in various bone-related procedures, including, but not limited to, fracture stabilization, plate stabilization, and bone reconstruction. While the device 100 as discussed above will be used as the exemplary device for purposes of describing the exemplary procedural steps below, any of the various device embodiments disclosed or contemplated herein can be used to perform the various bone-related procedures. As discussed elsewhere herein, in various implementations the device 100 can be provided as a combination device 100 with the fixation device 102 and the driver device 104 coupled together. More specifically, the device 100 can be packaged, shipped, stored, and ultimately removed from the packaging and prepared for use in a procedure in this coupled configuration, thereby simplifying the use of the device 100 by eliminating the need for the user to remove two different devices from their packaging and coupling them together before a procedure.

Once the combination device 100 is removed from the packaging and all preparations have been made for the desired procedure, the device 100 can be coupled to a known powered driver device (not shown), the distal tip 108 of the fixation device 102 positioned at the target location on the bone, and the powered driver device can be actuated to drive the fixation device 102 into the bone such that the proximal head 110 is driven into contact with the bone and, in some implementations, driven distally into the bone such that the head 110 is embedded into the bone such that the head 110 is flush with the surface of the bone. As discussed elsewhere herein, this step of driving the fixation device 102 into the bone is a single step process in which many of the required steps for known devices have been eliminated. That is, unlike known devices and related procedures, there is no need for measurement, pre-drilling, guide wire placement, over-drilling, tapping, counter-sink, using a screwdriver (unless adjustment is desired), cutting or capping the proximal end of the fixation device (as required with an olive wire), or subsequently having to remove the fixation device and insert permanent screw (as required with a k-wire). Instead, the combination device 100 allows for a one-step process in which the device 100 is coupled to the powered driver device (not shown), positioned as desired, and the fixation device 102 is urged into the target bone.

Thus, in certain implementations as mentioned above, the one-step procedure involves the combination device 100 being inserted into a target bone using a known powered driver device. In certain embodiments, a small guide hole can first be formed in the target bone using a known device and method. The sharp distal tip 108 of the fixation segment 102 is positioned in the guide hole and the powered driver device is attached to the driver segment 104 such that actuation of the wire driver device causes the driver segment 104 to rotate, thereby causing the attached fixation segment 102 to rotate. In one embodiment, the driver device rotates the device 100 in a clockwise direction. Alternatively, the small guide hole is not needed.

As the distal tip 108 penetrates the bone, the shaft 106 of the fixation segment 102 begins to penetrate the bone. As discussed above, in various implementations, the outer surface of the shaft 106 is threaded such that the threads 112 establish connection with the bone as the shaft 106 is rotated, thereby establishing "purchase" and causing the shaft 106 to penetrate. The small diameter of the fixation segment 102 (as discussed above) causes minimal bone removal or disruption. As the fixation segment 102 is inserted further, the proximal head 110 makes contact with the cortex of the bone (outer surface of the bone). Given its wider diameter in comparison to the shaft 106, the proximal head 110 provides compression against the surface of the bone. As such, the proximal head 110 provides advantages for fracture management (in comparison to K-wires and other fixation wires without a head or "olive"), as two fragments of bone can be held with any of the fixation device embodiments herein and compression between the two fragments can be achieved. Alternatively, the implant can also be used to temporarily secure two bone fragments at a fusion site before permanent fixation is delivered.

In one embodiment, the powered driver device can be a TPX® Universal Driver, which is commercially available from Stryker. Alternatively, the powered driver device can be any such known powered device (such as any of the drivers from Depuy Synthes, Hall, etc.) for coupling to a temporary or permanent fixation device and driving such a fixation device into a target bone during any bone procedure as contemplated herein.

Once the fixation segment 102 has been advanced to the point that proximal head 110 makes contact with the cortex of the bone, the segment 102 can be advanced such that the proximal head 110 is sunk or otherwise embedded into the bone. In certain embodiments, the head 110 can be advanced into the bone such that the proximal side 110B of the head 110 is flush with the surface of the bone or is otherwise not protruding from the bone. Further, according to various implementations, the distal side 110A of the proximal head 110 has cutting flutes (not shown) defined therein in (or otherwise disposed thereon) that allow the head 110 to be countersunk into the bone. Alternatively, the head 110 can have any other known mechanism or feature that makes it possible to embed the head 110 into the bone. At this point, the driver segment 104 can be detached from the fixation segment 102, leaving solely the embedded fixation segment 102 with nothing protruding above the surface of the bone. In contrast, with a traditional olive wire, even after some proximal portion of the olive wire is cut or bent, the wire will typically have at least the standard olive protruding from the bone and often at least a portion of the proximal wire protruding further. Alternatively, in certain implementations in which the device 100 is being used for temporary fixation, the proximal head 110 need not be embedded such that it is flush with the surface of the bone. The driver segment 104 can be detached by simply moving the driver segment 104 in a proximal direction to disengage the coupling feature 122 of the driver segment 104 from the coupling feature 114 of the fixation segment 102.

Once the fixation segment 102 is implanted as desired, the next step can depend on the success of the insertion of the segment 102, the type of procedure, and/or whether the segment 102 is going to be removed or implanted permanently. For example, if the surgeon is not satisfied with the insertion or the resulting position of the fixation segment 102, the surgeon can use the driver segment 104 to adjust the tension, depth, or position of the fixation segment 102. In other words, if the surgeon wants to "loosen" or otherwise retract the fixation segment 102 some length, the surgeon can reattach (or maintain attachment of) the driver segment 104 and, in certain implementations, use the powered driver tool to rotate the driver segment 104 (and thus the fixation segment 102) in the opposite direction, thereby causing the fixation segment 102 to move proximally in relation to the bone, thereby causing the segment 102 to retract. Alternatively, if the surgeon wants to "tighten" or otherwise cause the fixation segment 102 to be inserted further into the bone, the surgeon can use the driver tool to rotate the driver segment 104 (and thus the fixation segment 102) in the same direction as during insertion, thereby causing the fixation segment 102 to penetrate more deeply into the bone. In a further alternative, if the surgeon has completed the remainder of the bone correction procedure (including insertion of permanent fixation screws, for example) and does not intend to retain the fixation segment 102 in the bone, the surgeon can then reattach the driver tool to the driver segment 104 and use it to fully retract the fixation segment 102 by urging the driver segment 104 (and thus the fixation segment 102) in the opposite direction until it is fully retracted from the bone. In contrast, various known devices (such as K-wires, snap-off screws, and the like) cannot be loosened, tightened or easily removed via a detachable driver such as that described herein.

According to certain procedural implementations, any device embodiment herein can be used to secure a fixation plate to a bone. For example, the fixation plate (not shown) can be positioned in contact with the target bone area as desired and the device (such as device 100) can be inserted through an opening in the plate. More specifically, the distal end 108 of the fixation segment 102 is inserted through the opening. At this point, both the device 100 and the plate can be more precisely positioned as desired. When the fixation segment 102 is advanced and penetrates the bone, eventually the proximal head 110 of the segment 102 comes into contact with the outer surface of the plate, thereby securing it firmly against the bone. In various embodiments, at this point, the plate position can be assessed (such as with an image intensifier, for example) to ensure the desired position in the body. If it is determined as a result of this assessment that the plate position is not ideal, the device 100 can be retracted as described, the plate can be re-positioned, and the process can be repeated.

In certain embodiments as mentioned above, the fixation segment 102 can be left in the bone as a permanent implant. The ability to insert the segment 102 so that the proximal head 110 is flush with the external bone surface and then remove the driver segment 104 makes it possible for the fixation segment 102 to be a permanent fixation device. As such, according to some implementations, the device 100 can be used as a hybrid fixation construct, because it can be used permanently in combination with other fixation screws and/or fixation plates. For example, one or more devices 100 can serve as additional points of fixation across the surface of a fixation plate with minimal added time or expense.

In any use or method embodiment disclosed or contemplated herein, the device 10 can be provided with the fixation segment 12 and the driver segment 14 detachably coupled together for immediate use. Further, in some exemplary embodiments, the device 10 can be provided in this coupled configuration in the packaging in which it is delivered to the procedural arena (such as an operating room, for example) such that the fixation segment 12 and driver segment 14 are detachably coupled together when the device 10 is removed from the packaging by the surgeon or other user.

The various device embodiments disclosed or contemplated herein allow a surgeon to insert the device 10 into bone with the ease of a standard K-wire or olive wire while also allowing the surgeon to detach and, in some cases, reattach, the driver segment 14 for ease of operation, adjustment, or removal. Further, as mentioned above, the implementations herein do not require the various steps of a fixation screw (including pre-drilling, over drilling, depth measurement, counter sinking, tapping for insertion, etc.). In addition, the fixation device 10 embodiments herein allow various bone fixation procedures to be performed as described herein without the risk of obstructive bent, clipped, or long wires or sharp wires as is common with standard olive wires.

In certain implementations, a device can be used to help maintain the detachable coupling between the driver device and the fixation device during transport of the driver and fixation devices and prior to and during use. For example, FIGS. 9A-9H depict an attachment stabilization device 130 that can be coupled to and thereby help to maintain the coupling of a driver device 134 to a fixation device 132, thereby forming a three-piece combination device 128 as will be discussed in additional detail below. The driver device 134 represents any of the driver device embodiments disclosed or contemplated herein, and the fixation device 132 represents any of the fixation device embodiments disclosed or contemplated herein.

The driver device 134 and fixation device 132 can be disposed through a lumen 131 defined within the stabilization device 130 as shown in FIGS. 9A-9H such that the driver device 134 and fixation device 132 are coupled to each other within the lumen 131, resulting in the three-piece combination device 128 mentioned above. As such, the distal end of the fixation device 132 (including the distal tip 136) extends out of the lumen 131 and out of the distal end of the stabilization device 130 while the distal end of the driver device 134 (including the distal head 138 and male coupling feature 140) is disposed within the lumen 131 of the stabilization device 130 and coupled to the proximal head 142 such that the male coupling feature 140 is disposed within and coupled with the female coupling feature 144. More specifically, when the stabilization device 130 is positioned over the driver 134 and fixation 132 devices to stabilize and/or help to maintain the attachment of the two devices 134, 132 as shown, the distal end of the fixation device 132 extends out of a distal opening 146 in the stabilization device 130 and the driver device 134 is disposed through a proximal opening 148 in the stabilization device 130. Both the distal and proximal openings 146, 148 are in fluidic communication with the lumen 131 such that the openings 146, 148 provide access thereto.

As mentioned above, the stabilization device 130 embodiment described herein is used to maintain the coupling between any of the driver and fixation device embodiments disclosed or contemplated herein. As such, the stabilization device 130 is used to maintain the driver (such as driver 134) and fixation device (such as fixation device 132) in a coupled configuration (the three-piece combination device 128) in a package, during transport, during storage, during sterilization, and/or prior to use in a procedure. In fact, in certain embodiments as discussed below, the stabilization device 130 can also be used in combination with the driver and fixation devices during the first steps of the procedure.

Of course, the stabilization device is not limited to use with the driver and fixation device embodiments herein.

That is, the various stabilization device embodiments disclosed or contemplated herein can be used to maintain the coupling and stability of any similar implants with a fixation device and a driver device or equivalent components.

FIGS. 10A-10H depict one exemplary embodiment of the stabilization device 130. The device 130 has an elongate body 150 with the lumen 131 defined therethrough as discussed above. The body 150 has a distal section 150A, a proximal section 150B, and, in certain embodiments as will be discussed in additional detail below, an expanded section 166 disposed between and coupling the distal section 150A and the proximal section 150B. In certain implementations, the stabilization device 130 has retention structures 160, 162 disposed within the lumen 131 to retain the driver device 134 and fixation device 132 in coupled connection with each other.

More specifically, according to one embodiment, the stabilization device 130 has at least two flexible proximal retention protrusions 160 disposed within the lumen 131. In certain implementations, the proximal retention protrusions 160 are disposed within the lumen 131 along the length of the lumen 131 such that they are closer to the proximal opening 148 than they are to the distal opening 146. In the exemplary embodiment as best depicted in FIGS. 9F, 9G, 9H, 10D, 10F, and 10H, the stabilization device 130 has four proximal retention protrusions 160 disposed around the circumference of the lumen 131 and extending radially from the inner wall of the lumen 131 toward the center of the lumen 131 as shown. As best shown in FIGS. 9F-9H, the inner diameter of the opening defined by the proximal protrusions 160 is smaller than the outer diameter of the distal head 138 of the driver device 134. As such, the proximal protrusions 160 help to retain the distal head 138 of the driver device 134 within the lumen 131 of the device 130 as shown in FIGS. 9F and 9G. Further, in certain embodiments, the protrusions 160 are radially flexible and/or compressible such that the distal head 138 of the driver device 134 (and/or any other device with a greater outer diameter than the inner diameter defined by the protrusions 160) can be urged past the protrusions 160 if sufficient external force is applied to the driver device 134 to urge the distal head 138 past the protrusions 160.

Figures 9A, 9B, 9C, 9D:
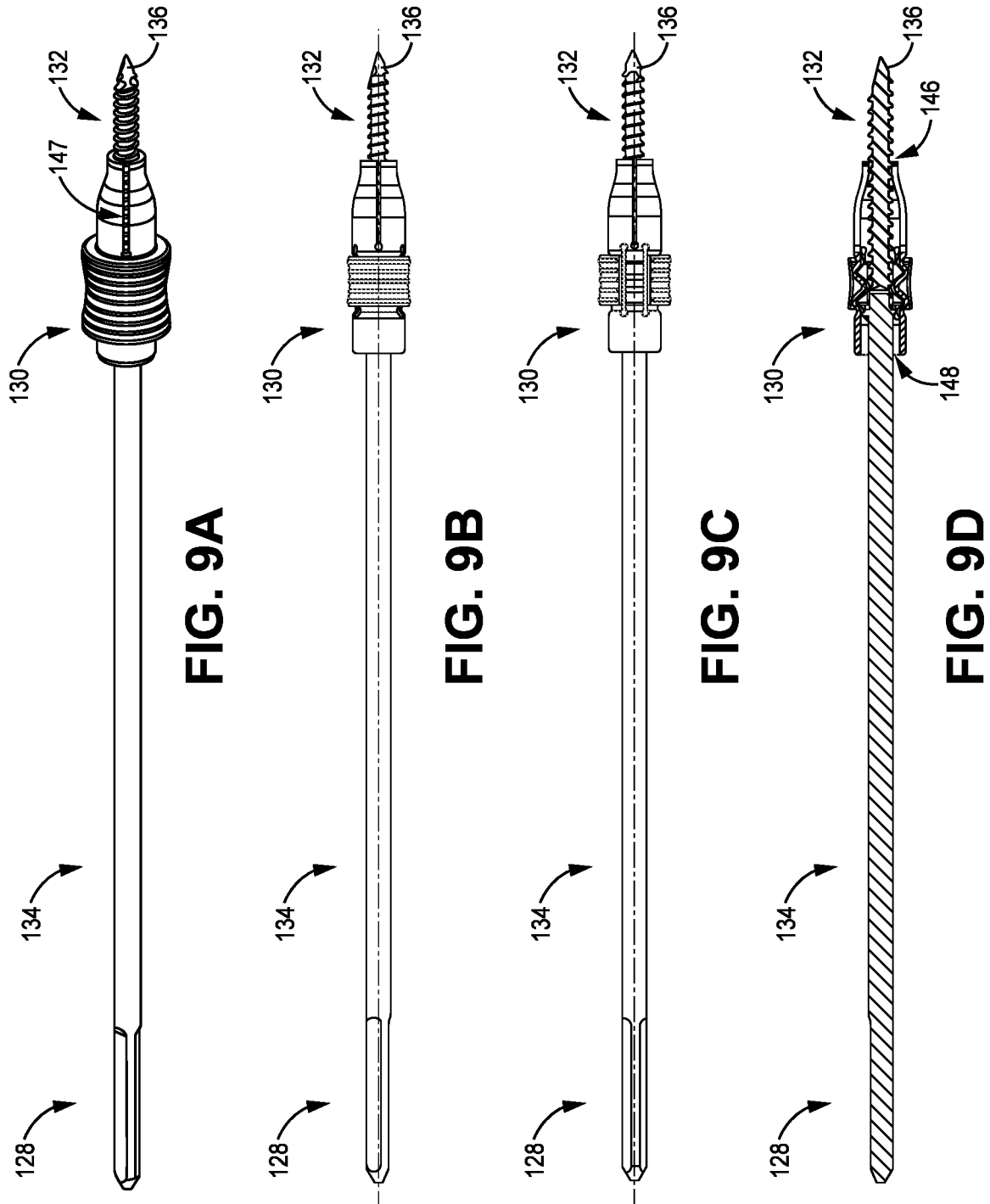
FIG. 9A is a perspective view of a stabilization device coupled to a combination device including a detachable driver device and a fixation device, according to one embodiment.
FIG. 9B is a side view of the stabilization device coupled to the combination device of FIG. 9A, according to one embodiment.
FIG. 9C is another side view of the stabilization device coupled to the combination device of FIG. 9A, according to one embodiment.
FIG. 9D is a cross-sectional view of the stabilization device coupled to the combination device of FIG. 9A, according to one embodiment.
Figure 10A:
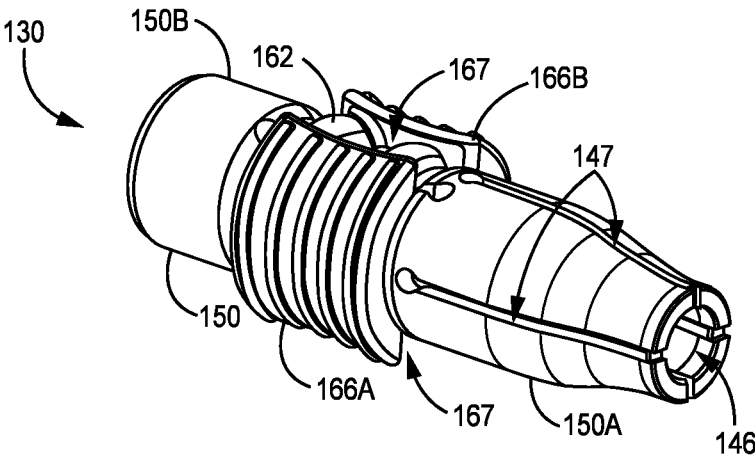
FIG. 10A is a perspective view of a stabilization device, according to one embodiment.
Figure 10B:
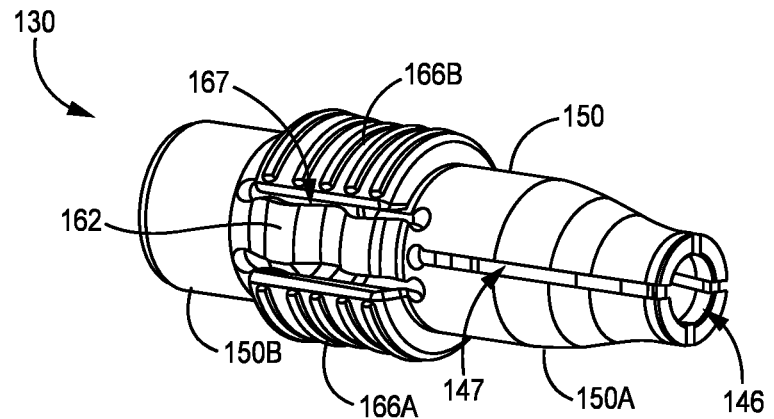
FIG. 10B is a another perspective view of the stabilization device of FIG. 10A, according to one embodiment.
Figure 10C:
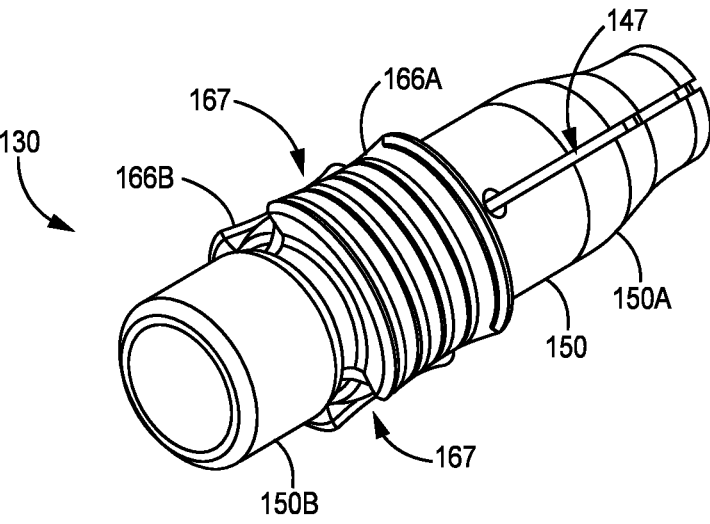
FIG. 10C is a another perspective view of the stabilization device of FIG. 10A, according to one embodiment.
Figure 10D:
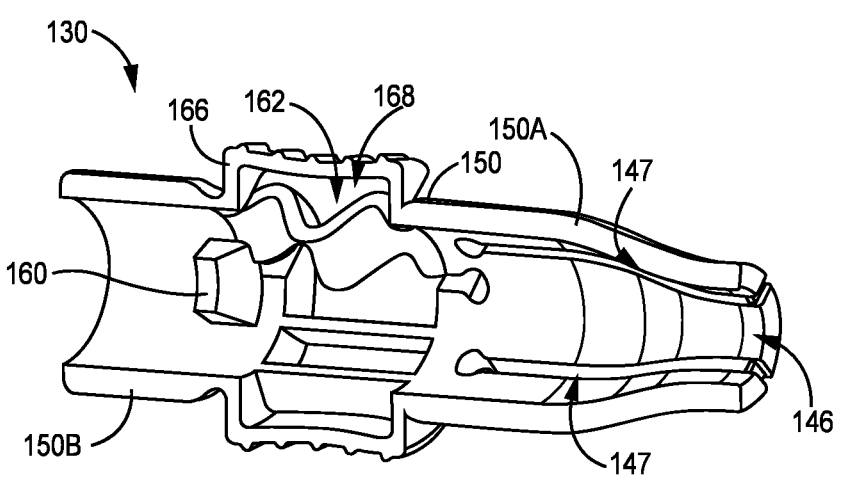
FIG. 10D is a cross-sectional perspective view of the stabilization device of FIG. 10A, according to one embodiment.
Figure 10E:
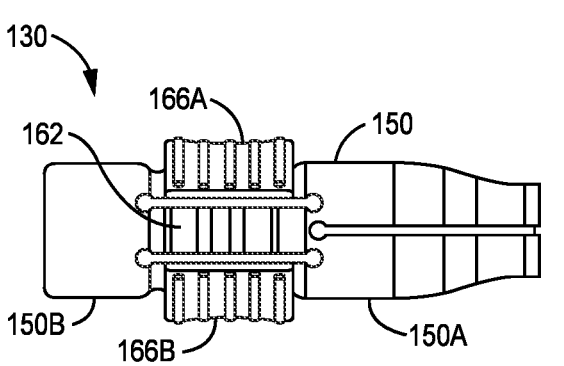
FIG. 10E is a side view of the stabilization device of FIG. 10A, according to one embodiment.
Figure 10G:
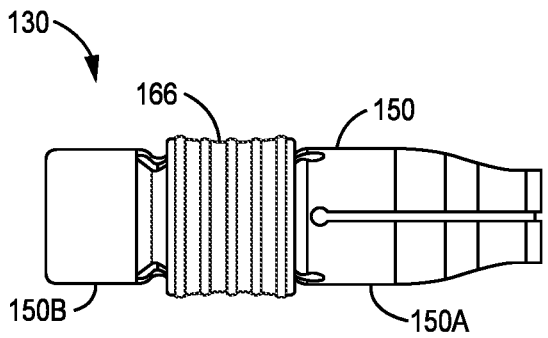
FIG. 10G is another side view of the stabilization device of FIG. 10A, according to one embodiment.
Figure 10F:
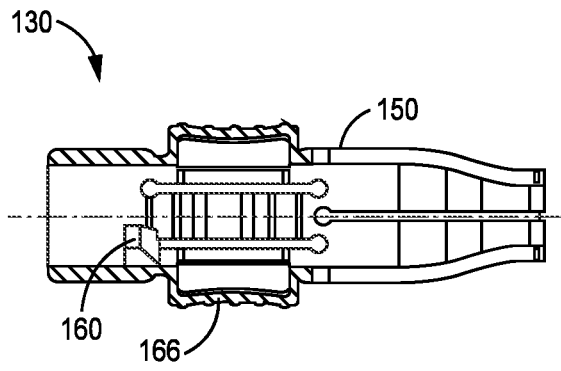
FIG. 10F is a cross-sectional side view of the stabilization device of FIG. 10E, according to one embodiment.
Figure 10H:
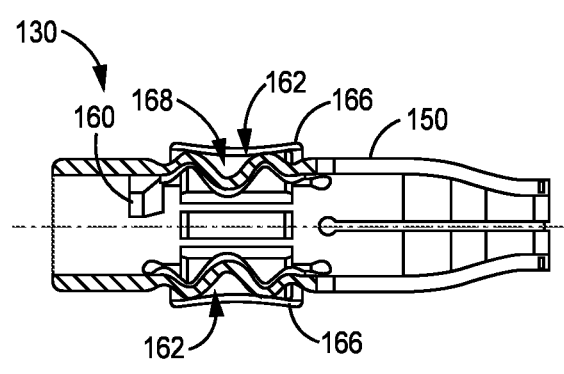
FIG. 10H is a cross-sectional side view of the stabilization device of FIG. 10G, according to one embodiment.

Further, the stabilization device 130 can also have at least two flexible distal retention structures 162 disposed within the lumen 131. According to certain embodiments, the distal retention structures 162 are disposed within the lumen 131 along the length of the lumen 131 such that they are disposed distally of the proximal protrusions 160. In the exemplary embodiment as best depicted in FIGS. 9F, 10D, and 10H, the stabilization device 130 has two distal retention structures 162 disposed on opposing sides of the lumen 131 and extending radially toward the center of the lumen 131 as shown. More specifically, in the exemplary implementation of FIGS. 9A-10H, the two distal retention structures 162 are flexible bellows 162 that extend axially between the distal section 150A and the proximal section 150B and have at least one fin 164 of the bellows 162 that extends radially toward the center of the lumen 131 as shown. More specifically, the distal end of the bellows 162 is attached to (or integral with) distal section 150A and the proximal end of the bellows 162 is attached to (or integral with) proximal section 150B as best shown in FIGS. 10D and 10H. Thus, the inner diameter of the opening defined by the distal retention structures 162 (in this case, the fins 164) is smaller than the outer diameter of the proximal head 142 of the fixation device 132. As such, the distal fins 164 help to retain the proximal head 142 of the fixation device 132 within the lumen 131 of the device 130 as shown in FIGS. 9F and 9G. Further, in certain embodiments, the fins 164 are flexible and/or compressible such that the proximal head 142 (and/or any other device or component with a greater outer diameter than the inner diameter defined by the fins 164) can be urged past the fins 164 if sufficient external force is applied to the fixation device 132 to urge the proximal head 142 past the fins 164. Alternatively, the fins 164 can be any type of protrusion 164 extending from a bellows or similar structure. In a further alternative, the distal retention structures 162 are not bellows, but instead are any type of retention structure, protrusion, or the like that can operate as described herein to assist with the stabilization of the driver device 134 and fixation device 132, including both axial and radial movement as discussed.

According to certain implementations, the distal opening 146 of the stabilization device 130 discussed above can also help to provide stabilization to the driver and fixation devices 134, 132. More specifically, in some embodiments, the distal opening 146 has an inner diameter that is sized to substantially match the outer diameter of the fixation device 132 (or the threads thereof). As such, when the fixation device 132 is positioned through the stabilization device 130 as described above, the inner diameter of the distal opening 146 is in contact with the outer diameter of the fixation device 132 such that that distal opening 146 provides support or stabilization to the fixation device 132 at the point along the length of the device 132 where it is in contact therewith.

Further, in accordance with some embodiments as best shown in FIGS. 9A, 9E, 10A, 10B, 10C, and 10D, the stabilization device 130 has longitudinal slits 147 defined along the length of the distal section 150A of the body 150. The slits 147 allow the distal section 150A to expand radially. For example, when the proximal head 142 of the fixation device 132 and/or the distal head 138 of the driver device 134 is urged distally through the distal section 150A as will be described in additional detail below, the slits 147 can allow the distal section 150A (and thus the lumen 131 therein) to expand radially and thereby allow the proximal head 142 and/or distal head 138 to pass therethrough.

As mentioned above, the stabilization device 130 can be used to help to maintain the coupling of the driver device 134 and the fixation device 132. With respect to maintaining the coupling of the two devices 134, 132, when the stabilization device 130 is positioned over the driver device 134 and the fixation device 132 as best shown in FIGS. 9F and 9G, the two retention structures 160, 162 are disposed on opposing sides of the coupled distal head 138 of the driver 134 and the proximal head 142 of the fixation device 132. More specifically, the proximal retention structures 160 are disposed proximally of the distal head 138 such that the retention structures 160 prevent the distal head 138 from moving proximally (and thus uncoupling from the proximal head 142) unless sufficient force is applied such that the head 138 can urge the structures 160 radially outward. Similarly, the distal retention structures 162 are disposed distally of the proximal head 142 such that the retention structures 162 prevent the proximal head 142 from moving distally (and thus uncoupling from the distal head 138) unless sufficient force is applied such that the head 142 can urge the structures 162 radially outward.

In addition, the stabilization device 130 can also be used to help to maintain the alignment of the longitudinal axes of the two devices 134, 132 while they are coupled. That is, the stabilization device 130 can help to prevent any radial movement of either of the devices 134, 132 in relation to each other. This radial movement restriction is achieved by the retention structures 160, 162 that are in contact with the devices 134, 132 at the coupling thereof as described above and by the inner diameter of the distal opening 146 of the device 130 that is in contact with the fixation device 132 as described above. Thus, the device 130 provides for stabilizing contact with the two devices 134, 132 at two different points along the length thereof: at the coupling of the distal head 138 and the proximal head 142 (via the retention structures 160, 162), and at a point along the length of the fixation device 132 distal of the proximal head 142 (via the distal opening 146).

The stabilization device 130 can also, in various embodiments, have an expanded section 166 on the elongate body 150 with a greater outer diameter than the rest of body 150, as shown. More specifically, the expanded section 166 is disposed between and attached to the distal section 150A and the proximal section 150B and extends radially outward from the body 150 further than either of those sections 150A, 150B as a result of the expanded section having a greater outer diameter. In certain implementations as is best shown in FIGS. 10A-10C, the expanded section 166 is actually made up of two sections 166A, 166B on opposing sides of the circumference of the device 130 such that the two sections 166A, 166B are separated by gaps 167. Further, in certain implementations, the bellows 162 are disposed within the gaps 167 as shown. In addition to making it easier for a user to grip the device 130, each of the expanded sections 166A, 166B forms a protective space for each of the bellows 162 that is defined circumferentially by the gap 167 in which the bellow 162 is disposed and radially by the space 168 created between the outer diameter of the expanded sections 166A, 166B and the bellows 162. Thus, each of the distal retention structures 162 is disposed within this protective space such that the structures 162 can expand or contract freely during use while preventing any force applied by the user grasping the expanded section 166 from being applied to the structures 162.

In use, the stabilization device 130 can be used in combination with any of the various combination device embodiments disclosed or contemplated herein to perform any of the bone-related procedures discussed above. While the device 130 with the driver device 134 and fixation device 132 as discussed above will be used as the exemplary device for purposes of describing the exemplary procedural steps below, the device 130 and reasonable variations thereof can be used with any of the various combination device embodiments disclosed or contemplated herein can be used to perform the various bone-related procedures. As discussed elsewhere herein, in various implementations the stabilization device 130 can be used to assist with keeping the fixation device 132 and the driver device 134 coupled together. Thus, in certain embodiments, the stabilization device 130 can be attached to or disposed around the fixation device 132 and the driver device 134 such that the stabilization device 130, the fixation device 132, and the driver device 134 form a three-piece combination device 128 that can be packaged, shipped, stored, and ultimately removed from the packaging and prepared for use in a procedure in the coupled configuration.

According to one embodiment, the first step is to attach the stabilization device 130 to the fixation device 132 and the driver device 134 to create the three-piece combination device 128. More specifically, the fixation device 132 and the driver device 134 are first coupled together as described elsewhere herein, and then the coupled devices 132, 134 are inserted into the stabilization device 130 (or, alternatively, the stabilization device 130 is inserted over the coupled devices 132, 134 and positioned over the coupling as described above). In one specific embodiment, the distal end 136 of the fixation device 132 is inserted distally through the proximal opening 148 of the stabilization device 130, through the lumen 131, and out of the distal opening 146 such that the fixation device 132 is urged distally through the device 130 until the proximal head 142 and the distal head 138 are both disposed between the distal and proximal retention structures 160, 162 as discussed above and depicted in FIGS. 9D, 9F, and 9G. That is, sufficient force is applied to the coupled devices 132, 134 such that the proximal head 142 and the distal head 138 are urged past the flexible proximal retention structures 160 in a manner discussed above. Once the coupled devices 132, 134 are positioned within the stabilization device 130 as intended to create the three-piece combination device 128, the three-piece combination device 128 can be packaged, shipped, stored, and ultimately removed from the packaging and prepared for use in a procedure in the coupled configuration.

Once the three-piece combination device 128 is removed from the packaging and all preparations have been made for the desired procedure, the driver device 134 can be coupled to a known powered driver device (not shown) in a manner similar to that described above. At this point, the surgeon (or other user) can hold the powered driver device in one hand and the three-piece combination device 128 in the other hand while positioning the distal tip 136 of the fixation device 132 at the target location on the bone. In one embodiment, the surgeon grasps the stabilization device 130 at the expanded sections 166A, 166B. Once the distal tip 136 is positioned as desired, the surgeon actuates the powered driver device to rotate the driver device 134 and the fixation device 132 and thereby urge the fixation device 132 into the bone. According to one embodiment, the stabilization device 130 maintains the coupling of the fixation device 132 and the driver device 134 while also preventing the tipping or radial movement of either device 132, 134 in relation to the other while the surgeon applies distal force to urge the fixation device 132 into the bone. In other words, the stabilization device 130 helps to ensure that the coupled devices 132, 134 travel their intended trajectory during the insertion process without either device 132, 134 tipping or moving radially in relation to the other. As the fixation device 132 advances into the bone, the stabilization device 130 also advances distally until the distal end of the stabilization device 130 contacts the bone surface. When the distal end of the stabilization device 130 contacts the bone surface, the stabilization device 130 stops advancing distally, while the driver device 134 and the fixation device 132 continue to advance. As such, the force applied by the powered driver device causes the proximal head 142 and the distal head 138 to continue to advance distally past the distal retention structures 162 and out of the distal opening 146 of the device 130, thereby causing the distal opening 146 to expand radially as a result of the slits 147 until the proximal head 142 and the distal head 138 exit the distal opening 146. This radial expansion of the distal end of the stabilization device 130 can, in certain embodiments, act as a visual indication to the surgeon that the proximal head 142 is in close proximity to the bone surface. Once the proximal head 142 and distal head 138 exit the device 130, the stabilization device 130 can be removed or moved aside such that the surgeon has full visualization of the proximal head 142 and the driver device 134 during the final implantation of the fixation device 132. According to certain embodiments, the remaining steps are similar to the embodiment of the device implantation process without the stabilization device discussed above.

While the various systems described above are separate implementations, any of the individual components, mechanisms, devices, or steps, and related features and functionality, within the various system embodiments described in detail above can be incorporated into any of the other system, device, or method embodiments herein.

The terms "about" and "substantially," as used herein, refers to variation that can occur (including in numerical quantity or structure), for example, through typical measuring techniques and equipment, with respect to any quantifiable variable, including, but not limited to, mass, volume, time, distance, wave length, frequency, voltage, current, and electromagnetic field. Further, there is certain inadvertent error and variation in the real world that is likely through differences in the manufacture, source, or precision of the components used to make the various components or carry out the methods and the like. The terms "about" and "substantially" also encompass these variations. The term "about" and "substantially" can include any variation of 5% or 10%, or any amount—including any integer—between 0% and 10%. Further, whether or not modified by the term "about" or "substantially," the claims include equivalents to the quantities or amounts.

Numeric ranges recited within the specification are inclusive of the numbers defining the range and include each integer within the defined range. Throughout this disclosure, various aspects of this disclosure are presented in a range format. It should be understood that the description in range format is merely for convenience and brevity and should not be construed as an inflexible limitation on the scope of the disclosure. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4¾. This applies regardless of the breadth of the range. Although the various embodiments have been described with reference to preferred implementations, persons skilled in the art will recognize that changes may be made in form and detail without departing from the spirit and scope thereof.

Although the various embodiments have been described with reference to preferred implementations, persons skilled in the art will recognize that changes may be made in form and detail without departing from the spirit and scope thereof.

What is claimed is:

1. A bone fixation device comprising:
   (a) a fixation segment comprising:
   (i) an elongate fixation shaft;
   (ii) a distal tip; and
   (iii) a proximal head comprising a first coupling structure, wherein the proximal head has a diameter that is greater than the diameter of the elongate fixation shaft;
   (b) a detachable driver segment comprising:
   (i) an elongate driver shaft; and
   (ii) a distal head comprising a second coupling structure, wherein the second coupling structure is detachably coupleable with the first coupling structure; and (c) a stabilization device removably coupleable to the fixation segment and the detachable driver segment, the stabilization device comprising:

(i) an elongate body comprising a lumen defined through the elongate body;

(ii) at least one distal flexible retention structure disposed within the lumen; and (iii) at least one proximal flexible retention structure disposed within the lumen proximally of the at least one distal flexible retention structure, wherein the stabilization device is positionable over the fixation segment and the detachable driver segment such that the proximal head and the distal head are disposed within the lumen between the at least one distal flexible retention structure and the at least one proximal flexible retention structure.

2. The device of claim 1, wherein the elongate fixation shaft comprises an outer surface having threads.

3. The device of claim 1, wherein the first coupling structure is a female coupling structure, and wherein the second coupling structure is a male coupling structure.

4. The device of claim 3, wherein the female coupling structure comprises an opening defined in the proximal head, wherein the male coupling structure comprises a ribbed protrusion extending from the distal head, and wherein the male coupling structure is mateable with the opening defined in the proximal head.

5. The device of claim 1, wherein the distal tip comprises a self-tapping tip.

6. The device of claim 1, wherein the proximal head further comprises an outer surface having threads.

7. The device of claim 1, wherein the detachable driver segment further comprises at least one attachment feature disposed in a proximal portion of the elongate driver shaft, wherein an actuable driver apparatus is removably attachable to the at least one attachment feature.

8. A bone fixation device comprising:

(a) a fixation segment comprising:

(i) an elongate uncannulated fixation shaft having a diameter of less than about 5 mm;

(ii) a sharp distal tip; and (iii) a proximal head comprising a first coupling structure, wherein the proximal head has a proximal flat surface comprising a diameter that is greater than the diameter of the elongate fixation shaft; and (b) a detachable driver segment comprising:

(i) an elongate driver shaft having a diameter of less than about 5 mm; and (ii) a distal head comprising a distal flat surface and a second coupling structure, wherein the second coupling structure is detachably coupleable with the first coupling structure and the distal flat surface is mateable with the proximal flat surface; and (c) a stabilization device removably coupleable to the fixation segment and the detachable driver segment, the stabilization device comprising:

(i) an elongate body comprising a lumen defined through the elongate body;

(ii) at least one distal flexible retention structure disposed within the lumen; and (iii) at least one proximal flexible retention structure disposed within the lumen proximally of the at least one distal flexible retention structure, wherein the stabilization device is positionable over the fixation segment and the detachable driver segment such that the proximal head and the distal head are disposed within the lumen between the at least one distal flexible retention structure and the at least one proximal flexible retention structure.

9. The device of claim 8, wherein the elongate fixation shaft comprises an outer surface having threads.

10. The device of claim 8, wherein the first coupling structure is a female coupling structure, and wherein the second coupling structure is a male coupling structure.

11. The device of claim 10, wherein the female coupling structure comprises an opening defined in the proximal flat surface of the proximal head, wherein the male coupling structure comprises a ribbed protrusion extending from the distal flat surface, and wherein the male coupling structure is mateable with the opening defined in the proximal flat surface.

12. The device of claim 8, wherein the sharp distal tip comprises a self-tapping tip.

13. The device of claim 8, wherein the proximal head comprises a distal surface having a curved convex shape, and wherein the distal head comprises a proximal surface having a curved convex shape.

14. The device of claim 8, wherein the proximal head further comprises an outer surface having threads.

15. The device of claim 8, wherein the detachable driver segment further comprises at least one attachment feature disposed in a proximal portion of the elongate driver shaft, wherein an actuable driver apparatus is removably attachable to the at least one attachment feature.

16. A bone fixation device comprising:

(a) a fixation segment comprising:

(i) an elongate uncannulated threaded fixation shaft having a diameter of less than about 5 mm;

ii) a sharp distal tip; and (iii) a proximal head comprising a first coupling structure, wherein the proximal head has a proximal flat surface comprising a diameter that is greater than the diameter of the elongate fixation shaft;

(b) a detachable driver segment comprising:

(i) an elongate driver shaft having a diameter of less than about 5 mm; and (ii) a distal head comprising a distal flat surface and a second coupling structure, wherein the second coupling structure is detachably coupleable with the first coupling structure and the distal flat surface is mateable with the proximal flat surface; and (c) a stabilization device comprising:

(i) an elongate body comprising a lumen defined through the elongate body;

(ii) at least one distal flexible retention structure disposed within the lumen; and (iii) at least one proximal flexible retention structure disposed within the lumen proximally of the at least one distal flexible retention structure, wherein the fixation segment and the detachable driver segment are positionable through the lumen of the stabilization device such that the proximal head and the distal head are coupled together and disposed between the at least one distal flexible retention structure and the at least one proximal flexible retention structure for transport, storage, and use of the bone fixation device.

17. The device of claim 16, wherein the first coupling structure is a female coupling structure, and wherein the second coupling structure is a male coupling structure.

18. The device of claim 17, wherein the female coupling structure comprises an opening defined in the proximal flat surface of the proximal head, wherein the male coupling structure comprises a ribbed protrusion extending from the distal flat surface, and wherein the male coupling structure is mateable with the opening defined in the proximal flat surface.

19. The device of claim 16, wherein the sharp distal tip comprises a self-tapping tip.

20. The device of claim 16, wherein the proximal head comprises a distal surface having a curved convex shape, and wherein the distal head comprises a proximal surface having a curved convex shape.

\* \* \* \* \*